United States Patent [19]  [11] Patent Number: 4,757,078
Misra  [45] Date of Patent: Jul. 12, 1988

[54] CYCLIC ARYL HYDROXAMIC ACIDS, DERIVATIVES THEREOF AND METHOD OF USE AS ANTI-ALLERGY AGENTS

[75] Inventor: Raj N. Misra, Hopewell, N.J.

[73] Assignee: E. R. Squibb & Sons, Inc., Princeton, N.J.

[21] Appl. No.: 936,064

[22] Filed: Nov. 28, 1986

[51] Int. Cl.⁴ .................. A61K 31/235; C07D 217/22
[52] U.S. Cl. .................................... 514/309; 546/141; 546/142
[58] Field of Search ................ 546/141, 142; 514/309

[56]  References Cited
U.S. PATENT DOCUMENTS 3,819,637  6/1974  Bell ........................................ 560/45
4,510,139  4/1985  Bailey ..................................... 560/45
4,515,980  11/1985  Bailey .................................... 560/45

FOREIGN PATENT DOCUMENTS 79141  10/1981  European Pat. Off. ................... 45/
81321  6/1983  European Pat. Off. .............. 560/45
122518  10/1984  European Pat. Off. ............. 560/45

OTHER PUBLICATIONS

Nair, Indian Journal of Chemistry, vol. 8, No. 10, pp. 949–950.
Jambuservala, Holt, Mason, Soc. 1931 373, 375.
I. G. Farbenind, D.R.P. 580519 [1932]; Frdl. 20 490.
Kehrmann, Neil, B. 47, 3102—Krystalle (aus Benzol).
Hey, Lawton, Soc. 1940 384, 387.
I. G. Farbenind, D.R.P. 530825 [1926]; Frdl. 18 604.
I. G. Farbenind, Schweiz.P. 135643 [1927].
I. G. Farbenind, D.R.P. 642549.
Borsche, Hahn, B. 82 [1949] 260, 262.
Burcherer, Stohmann, C. 1904 I, 1012,—Blattchen.
"Antiinflammatory 2-(Aminomethyl)Phenols. Structure–Activity Relationship", Itoh et al.
"Biochemical and Pharmacological Activities of Ono-3122, A Diuretic, and Ono-3144, A Novel Anti-Inflammatory Drug," Aishita et al.

Primary Examiner—Alan L. Rotman
Assistant Examiner—Robert C. Whittenbaugh
Attorney, Agent, or Firm—Lawrence S. Levinson; Burton Rodney

[57]  ABSTRACT

Cyclic aryl hydroxamic acids and derivatives thereof are provided having the structure

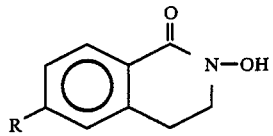

wherein R is H or arylalkyl, and including acid-addition salts thereof.

These compounds are useful as inhibitors of leukotriene production and as such are useful as antiallergy, anti-inflammatory and anti-psoriatic agents.

11 Claims, No Drawings

CYCLIC ARYL HYDROXAMIC ACIDS, DERIVATIVES THEREOF AND METHOD OF USE AS ANTI-ALLERGY AGENTS

DESCRIPTION OF THE INVENTION

The present invention relates to cyclic aryl hydroxamic acids and derivatives thereof which prevent leukotriene formation in macrophages and as such are useful, for example, as antiallergy agents, anti-inflammatory agents and in the treatment of psoriasis. These compounds have the structural formula

I wherein R is H or arylalkyl and including pharmaceutically acceptable salts thereof.

As to the pharmaceutically acceptable salts, those coming within the purview of this invention include the pharmaceutically acceptable acid-addition salts. Acids useful for preparing these acid-addition salts include, inter alia, inorganic acids, such as the hydrohalic acids, (e.g., hydrochloric and hydrobromic acid), sulfuric acid, nitric acid and phosphoric acid, and organic acids such as maleic, fumaric, tartaric, citric, acetic, benzoic, 2-acetoxybenzoic, salicylic; succinic acid, theophylline, 8-chlorotheophylline, p-aminobenzoic, p-acetamidobenzoic or methanesulfonic.

In addition, a method is provided for treating asthma mediated by leukotrienes in a mammalian species in need of such treatment, which method includes the step of administering to a mammalian host an effective amount of a compound of formula I or a pharmaceutically acceptable salt thereof.

Thus, compounds of formula I of the invention include compounds of the following structures:

II

III

The term "arylalkyl" as employed herein has the structure aryl-$(CH_2)_x$— wherein x is an integer from 1 to 10 and preferably from 2 to 6 and may include 1 or 2 lower alkyl substituents, such as $$-CH-, -CH-, -C-, (CH_2)_2-C-, CH_2CH_2, -CH_2CH-,$$
$$\phantom{xx}|\phantom{xxxx}|\phantom{xxxxx}|\phantom{xxxxxxx}|\phantom{xxxxxxxxxxxxxxx}|$$
$$\phantom{xx}CH_3\phantom{xx}C_2H_5\phantom{xx}CH_3\phantom{xxxx}CH_3\phantom{xxxxxxxxxxxxx}CH_3$$

$$-CH_2CH-, CHCH_2-, -CHCH-, -C-CH_2-,$$

$(CH_2)_3$, $(CH_2)_4$, $(CH_2)_5$, $(CH_2)_6$, $(CH_2)_7$, $(CH_2)_8$, $$-(CH_2)_2-CH-, -CH_2-C-, -CH_2-CH-CH-CH_2,$$

$$-CH_2-CH-CH_2-CH-, \text{ and the like.}$$

The term "lower alkyl" or "alkyl" as used herein refers to straight and branched chain radicals of up to 12 carbons and preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof.

The term "aryl" or "Ar" as employed herein as part of the arylalkyl group refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, 1 or 2 lower alkoxy groups and/or 1 or 2 hydroxy groups.

Thus, the term "aralkyl", "arylalkyl" or "aryl-lower alkyl" as used herein includes, for example, phenylethyl, phenylpropyl, phenylbutyl, phenylpentyl and the like.

Compounds of formula I are prepared by treating a cooled solution of an amide of the structure IV

IV (wherein Prot. represents a protecting group such as tetrahydropyranyl) in an organic solvent such as tetrahydrofuran, ethyl ether or benzene with a solution of butyllithium (preferably n-butyllithium) in hexane, warming the reaction to room temperature, cooling to from about −100° to about −78° C., treating the reaction mixture with ethylene oxide solution in tetrahydrofuran and then boron trifluoride etherate and maintaining the reaction mixture at a temperature of from about −100° to −78° C. to form alcohol V

V and treating V in benzene with sodium hydride or other base, such as potassium hydride or potassium bis(trimethylsilyl)amide in the presence of tosyl chloride to form the compound VI

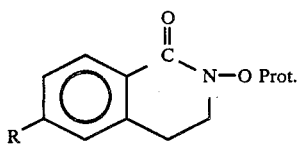

VI

Compound VI is treated with an acid such as pyridinium p-toluene sulfonic acid or hydrochloric acid in aqueous methanol or ethanol or other alcohol under mild heating (from about 40 to about 65° C.) to form compound I.

Starting compound IV wherein R is H, that is

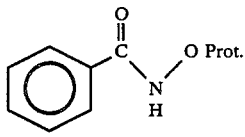

IVA may be prepared, for example, where Prot. represents tetrahydropyranyl, by treating O-tetrahydropyran-2-yl hydroxylamine (prepared as described in Example 2, Part A of U.S. Pat. No. 4,607,053) with benzoyl chloride in the presence of weak organic base such as triethylamine or pyridine, and methylene chloride or other solvent, such as ethyl ether or benzene.

Starting compound IV wherein R is arylakyl, that is IVB

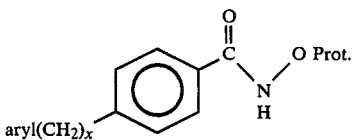

IVB may be prepared by treating a bromo compound of the structure VII

 aryl—(CH$_2$)$_{x-1}$Br  VII with triphenylphosphine to form compound VIII aryl—(CH$_2$)$_{x-1}$—P(C$_6$H$_5$)$_3$Br  VIII which is dissolved in a solvent such as tetrahydrofuran, ethyl ether or benzene, cooled to −20° to 0° C., and treated under inert atmosphere (such as argon), with potassium-t-amylate and methyl 4-formylbenzoate, A, that is

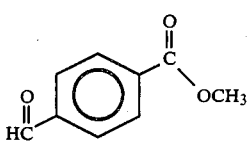

A in th organic solvent described above, (that is, tetrahydrofuran, ethyl ether or benzene) to form IX

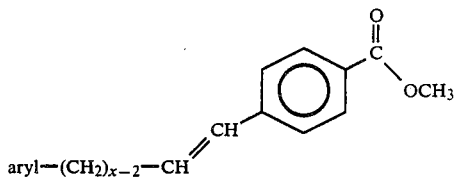

IX

Compound IX is then hydrogenated by treatment with hydrogen in the presence of a palladium on carbon catalyst to form X

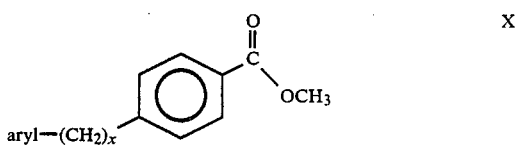

X

Compound X is then hydrolzed to the corresponding acid XI by treating X with strong base such as alkali metal hydroxide (for example, NaOH or LiOH) in the presence of aqueous methanol and organic solvent, such as tetrahydrofuran, to form acid XI

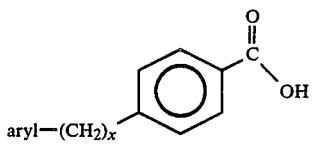

XI which is then protected, for example, by reacting with O-tetrahydropyran-2-yl hydroxylamine in the presence of dicyclohexnyl carbodiimide and hydroxy benzotriazole monohydrate to form VB (wherein the protecting group is tetrahydropyranyl).

The compounds of the invention are inhibitors and prevent leukotriene formation in macrophages (Samuelsson, B., Science, vol. 220, p. 568–575, 1983). The administration of compounds of this invention to humans or animals provides a method for treating allergy of a reagin or non-reagin nature. Asthma is preferably treated but any allergy wherein leukotrienes are thought to be involved as pharmacological mediators of anaphylaxis can be treated. For example, the compounds of this invention can be used for treatment of such conditions as allergic rhinitis, food allergy and utricaria as well as asthma.

An effective but essentially non-toxic quantity of the compound is employed in treatment.

The compounds of the invention can be administered orally or parenterally to various mammalian species known to be subject to such maladies. e.g., humans, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of the invention. Unless otherwise indicated, all temperatures are expressed in °C. TLC plates were visualized by spraying and heating with 5% phosphomolybdic acid in ethanol.

EXAMPLE 1

3,4-Dihydro-2-hydroxy-6-(4-phenylbutyl)-1(2H)-isoquinolinone

A.

N-(Tetrahydropyran-2-yloxy)-4-(4-phenylbutyl))benzamide (1) 3-Phenylpropyl triphenylphosphonium bromide A magnetically stirred suspension of 1bromo-3-phenylpropane (Aldrich, 13.7 ml, 90 mmol) and triphenylphosphine (47.2 g, 180 mmole) was heated at 100° C. (Oil bath) for 2.0 hours. The resulting while solid was then cooled and triturated with ether (5X) to remove most of the unreacted triphenylphosphine, to give Part A(1) compound in 96% yield (wt. 40.0 g).

(2) 4-(Phenyl-1-butenyl)benzoic acid, methyl ester

To a 0° solution of Part A (1) compound (3.55 g, 1.25 eq) in 30 ml of dry THF under Argon was added K-t-amylate (3.9 ml, 1.1 eq). After stirring for 30 minutes at 0° C. then allowing to warm to room temperature, a solution of methyl 4-formylbenzoate (1.0 g, 6.1 mmol, Fluka) in ~8 ml of dry THF was added dropwise. This solution was stirred for 3 hours at room temperature, then diluted with ~1 ml of $H_2O$, and concentrated to remove most of the THF. EtOAc (18 200 ml) was added and the mixture was washed with $H_2O$, 1N HCl (2X) and brine. After drying over anhydrous $MgSO_4$, the solvent was removed in vacuo to yield a yellow oil which solidified. Column purification of this crude product on silica gel eluted with 95:5 hexane/EtOAc yielded after concentration title aldehyde 1.5 g (93%) as a clear oil.

(3) 4-(4-Phenylbutyl)benzoic acid, methyl ester

To a stirring solution of Part A(2) ester (850 mg, 3.2 mmol) in 20 ml of $CH_3OH$ was added Pd/c (5%) 85 mg under Argon. Hydrogen gas was added and the reaction was allowed to stir under $H_2$ (balloon) for 1 hour. The mixture was filtered (millipore) and concentrated in vacuo to give title ester as a clear oil, 850 mg (~100%).

(4) 4-(4-Phenylbutyl)benzoic acid

A solution of Part A(3) compound (850 mg; 3.2 mmol), 2N NaOH (4.8 ml, 3.0 eq) in 35 ml of $CH_3OH$/THF (5:1) was heated to reflux for 2½ hours. The solution was acidified with 1N HCl (15 ml). THF was removed in vacuo and a white solid was collected by filtration. This solid was dissolved in ETOAc and washed with ½ saturated brine, then brine. After drying over anhydrous $MgSO_4$, concentration gave title acid 680 mg as a white solid. The filtrate, from the original filtration, was extracted with ETOAc 2X (75 ml portions) washed with ½ saturated brine, then brine. Concentration after drying over anhydrous $MgSO_4$ gave 80 mg of title acid, a total yield of 91%.

(5) N-(Tetrahydropyran-2-yloxy)4-(4-phenylbutyl)-benzamide

To a 0° C. solution of Part A(4) acid (700 mg, 2.8 mmol) in 40 ml of $CH_2Cl_2$ under Argon was added O-tetrahydropyran-2-ylhydroxylamine (prepared as described in U.S. Pat. No. 4,607,053, Example 2, Part A) (654 mg, 2.0 eq.), hydroxybenzotriazole hydrate (460 mg, 1.2 eq.), dicyclohexyl carbodiimide (700 mg, 1.2 eq.) sequentially. After 0.5 hour at 0° the solution was allowed to warm to room temperature and stir under Argon for 4 hours. The solution was filtered, concentrated in vacuo to yield a white solid which was chromatographed on LPS-1 silica gel eluting with 6:4 hexane/EtOAc. Product containing fractions were evaporated to give title compound as an oil, 1.0 g (~100%).

B. N-(Tetrahydropyran-2-yloxy)4-(4-phenylbutyl)2-hydroxyethylbenzamide

To a solution of 975 mg (2.76 mmol) of Part A(5) compound in 15ml of dry THF cooled in an ice-bath was added dropwise 2.5 ml (2.4M in hexane, 6.0 mmol, Alfa) of n-butyllithium solution. The reaction mixture was warmed to room temperature, stirred 15 minutes then cooled to −78°. To the resulting yellow-brown solution was added 1.5 ml (2.0M in THF, 3.0 mmol) of ethylene oxide solution followed by dropwise addition of 0.37 ml (3.0 mmol) of boron trifluoride etherate. The reaction mixture was stirred for 15 minutes at −78°, quenched with 1 ml of methanol, added to 60 ml of $H_2O$ and extracted with three 20 ml portions of ethyl acetate. The organic extracts were combined, dried ($MgSO_4$) and concentrated in vacuo to give a yellow oil. The crude material was purified by flash chromatography (15×5.0 cm, 2:1 EtOAc/petroleum ether) to afford 348 mg (32%) of title compound as a pale yellow oil.

270 MHz $^1H$ NMR ($CDCl_3$): δ1.66 (m, 11H, $PhCH_2(CH_2)_2$—, —$OCH_2(CH_2)_3$— of THP ring, —OH); 2.63 (m, 4H, benzylic —$CH_2$—); 2.97 (t, J=4, 1H, —$CH_2CH_2OH$); 3.08 (t, J 5, 1H, —$CH_2CH_2OH$); 3.66 (m, 1H, —$OCH_2$— of THP ring); 3.94 (m, 3H, —$OCH_2$— of THP ring, —$CH_2OH$); 5.14 (s, 1H, THP methine); 7.00-7.45 (m, 8H, aromatic); 9.34 (s, 1H, —NH—).

MS (CI); 398 (M+H).

TLC: $R_f$ (Silica gel, 2:1 ETOAc/petroleum ether)=0.23, PMA and UV.

C.

3,4-Dihydro-2-(tetrahydropyran-2-yloxy)-6-(4-phenylbutyl)-1-(2H)-isoquinolinone

To a solution of 318 mg (0.80 mmol) of Part B compound in 5 ml of dry benzene was added 78 mg (48% in oil, 1.6 mmol) of sodium hydride dispersion; then after 5 minutes, 153 mg (0.80 mmol) of recrystallized tosyl chloride was added. The reaction mixture was stirred for 16 hours then an additional 50 mg (1.0 mmol) of sodium hydride dispersion and 50 mg (0.26 mmol) of tosyl chloride were added. The resulting slurry was stirred for an additional 4 hours, added to 1 5 ml of $H_2O$ and extracted with two 10 ml portions of ethyl acetate. The combined organic extracts were dried ($MgSO_4$) and concentrated in vacuo to give an oil. The crude oil was purified by flash chromatography (10×3.0 cm, 1:1:5 EtOAc/$CHCl_3$/petroleum ether) to afford 190 mg (63%) of title compound as a pale yellow solid, m.p. 62°-64° C.

Partial 60 MHz $^1H$ NMR ($CDCl_3$) δ: 3.38-4.38 (m with T, J=6, at δ 3.92, 4H, —$OCH_2$— of THP ring and triplet corresponding to —$NCH_2$—); 5.25 (m, 1H, THP methine); 6.85-7.45 (m, 7H, aromatic ); 8.07 (d, J=8, 1H, aromatic C8 proton).

MS (CI); 296 (M+H−OTHP)+.

TLC: $R_f$ (silica gel, 2:2:5 $CHCl_3$/EtOAc/petroleum ether)=0.44, PMA and UV.

D.
3,4-Dihydro-2-hydroxy-6-(4-phenylbutyl)-1(2H)-isoquinolinone

A solution of 180 mg (0.47 mmol) of Part C compound, 130 mg (0.52 mmol, Aldrich) of pyridinium p-toluenesulfonic acid and 5 drops of $H_2O$ in 5 ml of methanol was refluxed for 3 hours. The reaction mixture was cooled, concentrated in vacuo and the residue added to 15 ml of ethyl acetate. The solution was washed with 15 ml of $H_2O$, dried ($Na_2SO_4$) and concentrated in vacuo to give a solid. Recrystallization (EtOAc/petroleum ether) of the solid afforded 90 mg (65%) of title product as a white powder, m.p. 82°–83°.

IR(KBr) 3429, 3062 (broad), 2933, 1648, 1626, 1613, 1570, 1483, 1453, 1333, 1247, 964, 698 cm$^{-1}$.

270 MHZ$^1$H NMR(CDCl$_3$) δ: 1.66 (m, 4H, —(CH$_2$)$_2$CH$_2$Ph) 2.64 (m, 4H, —CH$_2$(CH$_2$)$_2$CH$_2$Ph) 3.14 (dd, J=7, 7, 2H, —NHCH$_2$CH$_2$) 3.88 (dd, J=7, 7 2H, —NCH$_2$—) 6.98 (s, 1H, aromatic C5 proton) 7.10–7.35 (m, 6H, aromatic) 7.95 (d, J=8, 1H, aromatic C8 proton) 8.38 (br s, 1H, —OH).

MS (CI): 296 (M+H)$^+$.

TLC: R$_f$(silica gel, 1:9 MeOH/CH$_2$Cl$_2$)=0.61, PMA (faint) and UV.

Microanalysis calcd for C$_{19}$H$_{21}$NO$_2$: C, 77.26; H, 7.17; N, 4.74. Found: C, 76.95; H, 7.08; N, 4.80.

EXAMPLE 2
3,4-Dihydro-2-hydroxy-1(2H)-isoquinolinone

A. N-(Tetrahydropyran-2-yloxy)benzamide

To a solution of 1.00 g (8.55 mmol) of O-tetrahydropyran-2-ylhydroxylamine (prepared as described in U.S. Pat. No. 4,607,053, Example 2, Part A) and 1.4 ml (10 mmol) of sieve-dried triethylamine in 15 ml of dry CH$_2$Cl$_2$ cooled to −20 was added a solution of 1.50 g (10.7 mmol) of benzoyl chloride in 5 ml of CH$_2$Cl$_2$ over 10 minutes. The reaction mixture was stirred for 1 hour then diluted with 15 ml of ethyl acetate. The resulting slurry was filtered and the filtrate concentrated in vacuo to give a solid. Recrystallization (EtOAc/petroleum ether) of the solid afforded 1.45 g (77%) of title compound as white crystals, m.p. 130°–134°.

60 MHz $^1$H NMR (CDCl$_3$) δ: 1.40–2.10 (m, 6H, —OCH$_2$(CH$_2$)$_3$—THP ring); 3.40–4.30 (m, 2H, —OCH$_2$— of THP ring); 5.07 (m, 1H, THP methine); 7.10–7.90 (m, 5H, aromatic).

TLC: R$_f$ (silica gel, 1:1 EtOAc/petroleum ether)=0.42, UV and PMA.

B. N-(Tetrahydropyran-2-yloxy)-2-(hydroxyethyl)benzamide

To a solution of 490 mg (2.22 mmol) of Part A compound in 10 ml of dry tetrahydrofuran at 0° was added 2.0 ml (2.4M in hexane, 4.8 mmol), of n-butyllithium solution. The reaction mixture was warmed to room temperature, stirred for 30 minutes then cooled to −78°. To the resulting orange-yellow solution was added 1.8 ml (2M in tetrahydrofuran, 3.6 mmol) of an ethylene oxide solution followed by 0.45 ml (3.6 mmol, MCB) of boron trifluoride etherate. The reaction mixture was stirred for 15 minutes, quenched by adding to saturated aqueous NaHCO$_3$ then added to 40 ml of saturated aqueous NaCl solution and extracted with four 25 ml portions of ethyl acetate. The organic extracts were combined, dried (Na$_2$SO$_4$) and concentrated in vacuo to give an oil. The crude material was purified by flash chromatography (12×3 cm, 3:1 EtOAc/petroleum ether) to afford 285 mg (49%) of title compound as a pale yellow oil.

60 MHz $^1$HNMR(CDCl$_3$) δ: 1.20–2.15 (m, 6H, —OCH$_2$(CH$_2$)$_3$— of THP ring); 2.85 (t, J=6, 2H, benzylic methylene); 3.25–4.70 (m, 6H, —NH—, —CH$_2$OH, —OCH$_2$— of THP ring); 5.03 (br s, 1H, THP methine); 7.20 (m, 4H, aromatic).

MS(CI): 266 (M+H$^+$).

TLC: R$_f$ (silica gel, 2:1 EtOAc/petroleum ether)=0.18, PMA and UV.

C. 3,4-Dihydro-2-tetrahydropyran-2-yloxy-1(2H)-isoquinolinone

An oil dispersion of 130 mg (50%, 2.7 mmol, Alfa) of sodium hydride was washed several times with petroleum ether to remove the oil, then 5 ml of dry benzene was added, followed by a solution of 320 mg (1.21 mmol) of Part B compound in 5 ml of benzene. The reaction mixture was heated to 50° for 15 minutes, cooled to room temperature, then 275 mg (1.44 mmol) of recrystallized tosyl chloride was added. The slurry was stirred for 14 hours, added to 15 ml of 1M aqueous NaOH solution and extracted with two 10 ml portions of ethyl acetate. The organic extracts were combined, dried (MgSO$_4$) and concentrated in vacuo to afford an oil. The crude oil was purified by flash chromatography (12×3.0 cm, 1:4 EtOAc/petroleum ether) to afford 174 mg (58%) of title compound as a colorless oil.

60 MHz $^1$H NMR(CDCl$_3$) δ: 1.25–2.20 (m, 6H, —OCH$_2$(CH$_2$)$_3$— of THP ring); 3.20 (dd, J=3, 7, 2H, benzylic —CH$_2$—); 3.40–4.30 (m with t, J=6, at δ3.90, 4H, —NCH$_2$— and —OCH$_2$— of THP ring); 5.20 (m, 1H, THP methine); 7.27 (m, 3H, aromatic); 8.07 (dd, J=2, 6, 1H, aromatic).

TLC: R$_f$ (silica gel, 2:1 EtOAc/petroleum ether)=0.40, PMA and UV.

D. 3,4-Dihydro-2-hydroxy-1(2H)-isoquinolinone

A solution of 100 mg (0.40 mmol) of Part C compound and 110 mg (0.44 mmol) of pyridinium p-toluenesulfonate in 3 ml of methanol containing three drops of H$_2$O was refluxed for 3 hours. The reaction mixture was cooled, concentrated in vacuo and the residue partitioned between 10 ml of H$_2$O and 10 ml of ethyl acetate. The organic layer was separated and the aqueous phase was extracted with two additional 10 ml portions of ethyl acetate. The combined organic extracts were dried (Na$_2$SO$_4$) and concentrated in vacuo to give an oil. The crude oil was crystallized (EtOAc/petroleum ether) to afford 27 mg (42%) of title product as white crystals, m.p. 95°–96°.

IR(KBr) 3434, 3000 (broad), 1654, 1576, 1483, 1441, 1335, 1305, 1243, 961, 738, 687 cm$^{-1}$.

270 MHz$^1$H NMR(CDCl$_3$) δ: 3.20 (t, J=7, 2H, benzylic —CH$_2$—); 3.92 (t, J=7, 2H, —CH$_2$N—); 7.21 (d, J=7, 1H, aromatic C5 proton); 7.34 (dd, J=8, 8, 1H, aromatic C6 or C7 proton); 7.45 (dd, J=7, 7, aromatic C6 or C7 proton); 8.06 (d, J=6, 1H, aromatic C8 proton).

MS(CI): 164 (M+H)$^+$.

TLC: R$_f$ (silica gel, 1:19 MeOH/CH$_2$Cl$_2$)=0.31, PMA and UV.

Anal Calcd for C$_9$H$_9$NO$_2$: C, 66.25: H, 5.56; N, 8.58; Found: C, 65.97; H, 5.64; N, 7.98.

EXAMPLES 3 TO 17

Following the procedures as outlined in the Specification and the working Examples, the following additional compounds in accordance with the present invention may be prepared.

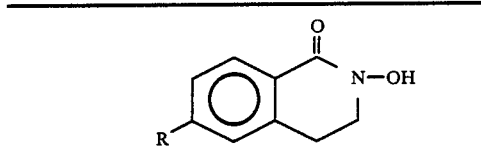

| Ex. No. | R |
|---|---|
| 4. | $C_6H_5CH_2-$ |
| 5. | $C_6H_5(CH_2)_2-$ |
| 6. | $C_6H_5(CH_2)_3-$ |
| 7. | $C_6H_5(CH_2)_5-$ |
| 8. | 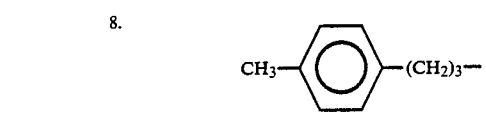 |
| 9. | 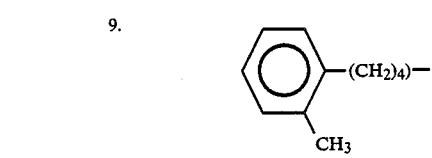 |
| 10. | 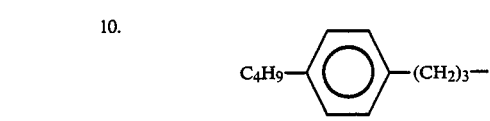 |
| 11. | 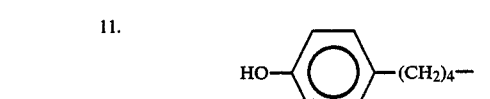 |
| 12. | 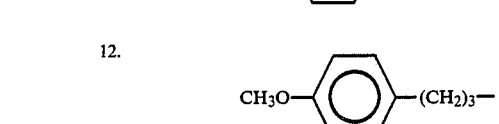 |
| 13. | 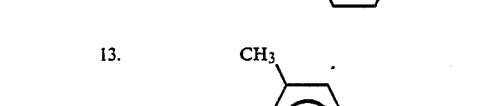 |
| 14. | 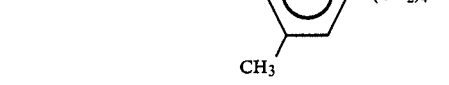 |
| 15. | 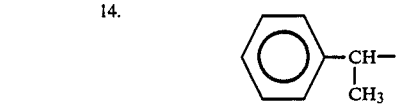 |

-continued

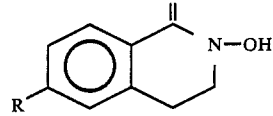

| Ex. No. | R |
|---|---|
| 16. | 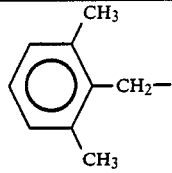 |
| 17. | 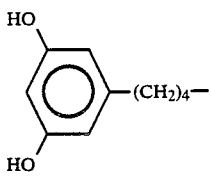 |

What is claimed is:

1. A compound having the structure

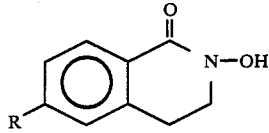

wherein R is H or arylalkyl, which has the structure aryl-$(CH_2)_x$—wherein x is 1 to 10 and aryl refers to a monocyclic or bicyclic aromatic group having from 6 to 10 carbons in the aromatic ring which may be unsubstituted or substituted with 1 or 2 lower alkyl groups, 1 or 2 lower alkoxy groups and/or 1 or 2 hydoxy groups; and alkyl or lower alkyl by itself or as part of another group refers to straight or branched chain radicals having 1 to 12 carbons, and including pharmaceutically acceptable acid-addition salts thereof.

2. The compound as defined in claim 1 wherein R is H.

3. The compound as defined in claim 1 wherein R is arylalkyl.

4. The compound as defined in claim 3 wherein R is aryl$(CH_2)_x$—wherein x is 2 to 6.

5. The compound as defined in claim 1 wherein R is phenylethyl, phenylpropyl or phenylbutyl.

6. The compound as defined in claim 1 having the name 3,4-dihydro-2-hydroxy-6-(4-phenylbutyl)-1(2H)-isoquinolinone.

7. The compound as defined in claim 1 having the same 3,4-dihydro-2-hydroxy-1(2H)-isoquinolinone.

8. A composition for inhibiting allergic conditions mediated by leukotrienes in a mammalian species, comprising an effective amount of a compound as defined in claim 1 or a pharmaceutically acceptable salt thereof, and a pharmaceutically acceptable carrier thereof.

9. A method of inhibiting leukotriene biosynthesis to treat inflammation or psoriasis, which comprises administering to the circulatory system of a mammalian host an effective amount of a compound as defined in claim 1.

10. The method as defined in claim 9 wherein said compound is administered in an amount within the range of from about 1 to about 100 mg/kg.

11. A method for treating asthma in a mammalian species in need of such treatment, which comprise administering to a mammalian host an effective amount of a compound as defined in claim 1.

* * * * *